United States Patent [19]

Matsuo et al.

[11] Patent Number: 4,633,882
[45] Date of Patent: Jan. 6, 1987

[54] DEVICE FOR DIAGNOSING BODY CAVITY INTERIORS WITH ULTRASONIC WAVES

[75] Inventors: Kazumasa Matsuo, Tama; Akio Nakada, Hachioji, both of Japan

[73] Assignee: Olympus Optical Co., Ltd., Tokyo, Japan

[21] Appl. No.: 778,763

[22] Filed: Sep. 23, 1985

Related U.S. Application Data

[63] Continuation of Ser. No. 475,601, Mar. 15, 1983, abandoned.

[30] Foreign Application Priority Data

Mar. 15, 1982 [JP] Japan ................. 57-40480

[51] Int. Cl.⁴ ............................................. A61B 10/00
[52] U.S. Cl. ........................................ 128/660; 128/4
[58] Field of Search ................. 128/4, 6, 660; 73/633, 73/634

[56] References Cited

U.S. PATENT DOCUMENTS

| | | | |
|---|---|---|---|
| 3,357,433 | 12/1967 | Fourestier et al. | 128/4 |
| 3,583,393 | 6/1971 | Takahashi | 128/4 |
| 3,643,653 | 2/1972 | Takahashi et al. | 128/6 |
| 4,305,386 | 12/1981 | Tawara | 128/4 |
| 4,321,915 | 3/1982 | Leighton et al. | 128/4 |
| 4,327,738 | 5/1982 | Green et al. | 128/660 |
| 4,341,205 | 7/1982 | Hosono et al. | 128/6 |
| 4,349,032 | 9/1982 | Koyata | 128/660 |
| 4,391,282 | 7/1983 | Ando et al. | 128/660 |

FOREIGN PATENT DOCUMENTS

| | | | |
|---|---|---|---|
| 2950203 | 6/1980 | Fed. Rep. of Germany | 128/660 |
| 53-85982 | 7/1978 | Japan | 128/660 |
| 57-156737 | 9/1982 | Japan | |
| 57-156738 | 9/1982 | Japan | |

Primary Examiner—Kyle L. Howell
Assistant Examiner—Ruth S. Smith
Attorney, Agent, or Firm—Armstrong, Nikaido, Marmelstein & Kubovcik

[57] ABSTRACT

A device for diagnosing body cavity interiors which comprises an elongated insertion portion for introduction into a body cavity. The insertion portion includes a guide tube extending along the length thereof with a window formed in the insertion portion at the end of the guide tube. An ultrasonic wave probe is positioned at the forward end of the insertion portion, the ultrasonic head transmitting ultrasonic waves to body tissue and receiving ultrasonic waves reflected from the body tissue. A curved portion is formed in the insertion portion at a position adjacent to the ultrasonic head. A optical tube is inserted into the guide tube wherein the forward end of the optical tube is positioned in the window of the insertion portion, such that the body tissue may be observed through the optical tube. Further, an optical tube fitting member is coupled to the rear of the insertion portion with the optical tube being inserted into the insertion portion through the fitting member. The axis of the guide tube is positioned to the right and above the axis of the insertion portion with reference to an observer looking through the optical tube and the guide tube is movable in the insertion portion such that the area of observation through the optical tube can be varied.

8 Claims, 17 Drawing Figures

DEVICE FOR DIAGNOSING BODY CAVITY INTERIORS WITH ULTRASONIC WAVES

This application is a continuation of application Ser. No. 475,601 filed Mar. 15, 1983 abandoned.

BACKGROUND OF THE INVENTION

This invention relates to a device for diagnosing body cavity interiors with ultrasonic waves wherein the observation can be made in a visual field which is little intercepted and can be well seen.

An ultrasonic wave diagnosing device wherein ultrasonic waves are transmitted and received to diagnose acoustic information within a body cavity has recently come to be used together with an endoscope wherein the inserted part is introduced into the body cavity so as to be able to optically observe the body cavity interior or to cure it by using a forceps. In this ultrasonic wave diagnosing device, when ultrasonic wave pulses are projected onto an object, for example, from the body surface and the projected ultrasonic waves propagate, they will be reflected by a discontinuous boundary surface of an acoustic impedance represented by the product of the density of the medium and the sound velocity, therefore the above mentioned reflected ultrasonic wave pulses will be received and the acoustic information related to the reflection intensity will be utilized for a diagnosis.

When compared with an X-ray device, an ultrasonic wave diagnosing device has many advantages such as information on a living body soft structure can be easily made without using a forming agent, the living body structure will not be destroyed by radioactive rays and the device is easier to handle and is less dangerous. Further, with the recent improvements of the quality and quantity of the information by the progress of the technique on ultrasonic waves, this device is becoming popular as a clinical diagnosing device in the medical field.

As compared to diagnosing wherein ultrasonic wave pulses are transmitted and received on the above mentioned body surface, in the method of diagnosing body cavity interiors with ultrasonic waves wherein ultrasonic wave pulses are transmitted and received at a position near a body organ within a body cavity, high frequency ultrasonic waves (comparatively) with large propagation attenuation can be transmitted and received and therefore there are the advantages that information of a disintegratability and high precision can be obtained and the method will not be influenced by a hypodermic fat layer or the like interposed between objects. Therefore, this method will be used more and more in the future. It is general that this ultrasonic wave diagnosing device to be used as introduced into a body cavity is used integrally with an endoscope as an optically observing means or as fitted with a removable endoscope (optical sighting tube).

Body cavity interior ultrasonic wave diagnosing device of this kind are already suggested in Japanese patent application Nos. 40813 and 40814/1981. In the body cavity interior ultrasonic wave diagnosing device of these prior arts, an incised window is formed on the outer periphery of the right side of an inserted part (as seen from the operator on the hand side in the normal use) in the rear of a curved part and an optical sighting tube is arranged so that an objective optical system at its tip may face the above mentioned incised window from the hand side of the inserted part and a visual field may be rightward from the incised window, because, particularly in the diagnosis of organs within an abdominal cavity, in which the abdominal wall has many blood vessels and the position the organ is determined, therefore the inserting position and inserting direction are medically determined. Therefore, if the visual field is rightward in the normal use, it will be sufficient. However, in the above mentioned prior arts, there have been disadvantages that, in case the elongate inserted part is introduced into a body cavity, the body tissue will contact the outer periphery of the side part from the lower part of the inserted part, the visual field of the optical sighting tube will be obstructed by the tissue and, with only a rightward visual field and curve, a dead angle will be produced for some organ and it will not be able to be diagnosed with ultrasonic waves in some position.

BRIEF SUMMARY OF THE INVENTION

An object of the present invention is to provide a device for diagnosing body cavity interiors with ultrasonic waves wherein, in case it is introduced into a body cavity, the visual field will not be intercepted by a surrounding organ or the like.

Another object of the present invention is to provide a device for diagnosing body cavity interiors with ultrasonic waves which can be contacted with body cavity interior positions in a wide range to enable the diagnosis with ultrasonic waves without producing a dead angle.

Further, another object of the present invention is to provide a device for diagnosing body cavity interiors with ultrasonic waves which can be variably set in the visual field direction adapted to the observation.

Other objects, features and advantages of the present invention will be made apparent enough with the following description.

BRIEF DESCRIPTION OF THE DRAWINGS

FIGS. 1 to 17 relate to an embodiment of the present invention.

DETAILED DESCRIPTION

Figure 1:
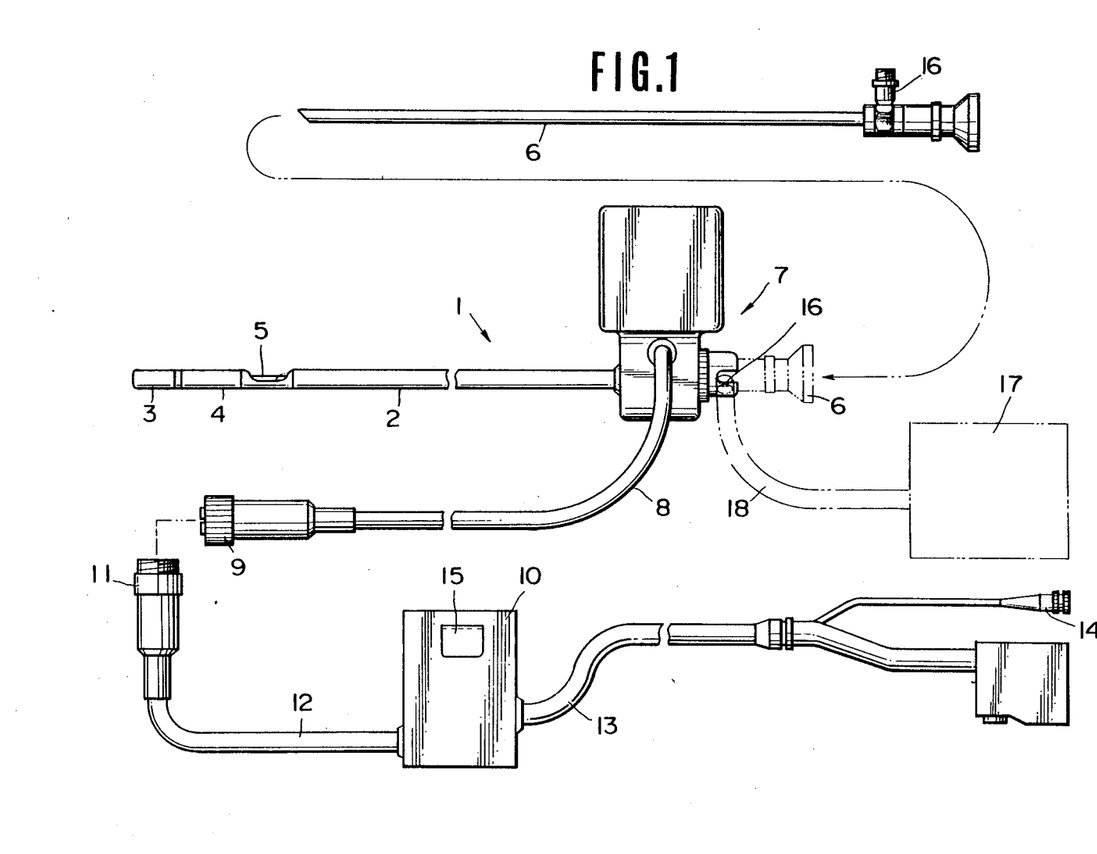
FIG. 1 is a general elevation of an ultrasonic wave diagnosing device.
Figure 2:
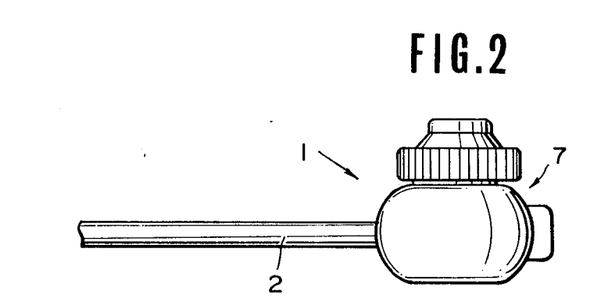
FIG. 2 is a plan view showing an operating part on the hand side of an ultrasonic wave probe body.

As shown in FIGS. 1 and 2, in an ultrasonic wave probe body 1, an ultrasonic wave probe head 3 having a function of transmitting and receiving ultrasonic waves and a curved part 4 are connected in turn from the front in the tip part of an elongate inserted part 2 to be introduced into a body cavity, an incised window 5 is provided on the upper side outer periphery of the inserted part 2 in the rear of this curved part 4. A guide tube has a diagonally sighting optical sighting tube 6 removably inserted therein. The optical sighting tube 6 has a visual field diagonally forward for example, by 45 degrees. The optical sighting tube 6 inserted is arranged from the rear end of the above mentioned inserted part 2 to the incised window 5. Further, an operating part 7 which is also a holding part is arranged on the hand side in the rear of the above mentioned inserted part 2 and a flexible electric cable 8 is connected and extended out of the side part of this operating part 7 and is fitted at the rear end with a connector 9 of a liquid-tight structure so as to be generally liquid-tight.

The above mentioned electric cable 8 is to be connected to a second electric cable 12 extended out of a pulse generating unit 10 (generating pulses fed to a later described ultrasonic wave oscillator within the ultrasonic wave probe head 3) and having a connector 11 at the tip. Also, a third electric cable 13 is extended out of the pulse generating unit 10 and is to be connected to a current source and ultrasonic wave indicating device not illustrated through a connector 14. In this embodiment, the electric cable 8 extended out of the above mentioned ultrasonic wave probe body 1 is not connected directly integrally with the pulse generating unit 10, because the entire ultrasonic wave probe body 1 including this electric cable 8 must be separated from the pulse generating unit 10 so as to be able to be dipped and sterilized in a sterilizing liquid. Further, the above mentioned electric cable 8 is not removably connected to the pulse generating unit 10 but is connected through the second electric cable 12 extended out of this pulse generating unit 10, because the electric cable 8 is a component part of the ultrasonic wave probe body to be in direct contact with the patient as mentioned above, must be entirely dipped and sterilized in a sterilizing liquid and will be inconvenient if it is long. Further, the above mentioned pulse generating unit 10 has a hanging hook 15 which is used to hang the unit 10 so that the electric cable 8 does not contact the floor or the like. A light guide connector 16 is provided to project on the hand side of the above mentioned optical sighting tube 6 so that a flexible light guide cable 18 connected to a light source 17 may be removably connected the endoscope.

Figure 3:
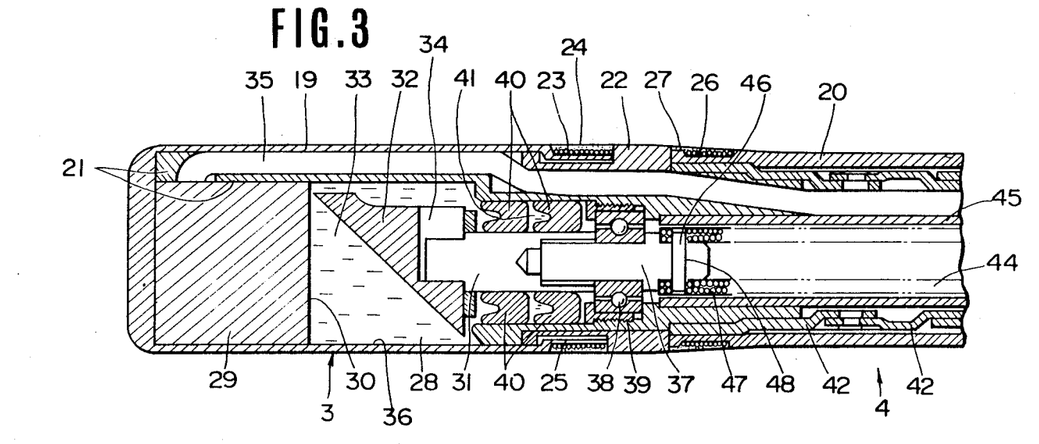
FIG. 3 is a magnified vertically sectioned view of the tip part of the ultrasonic wave probe body in FIG. 1.

The above mentioned ultrasonic wave probe head 3 and curved part 4 are formed as shown in FIG. 3. That is to say, the ultrasonic wave probe head 3 is covered on the tip side with such soft tubular jacket cover 19 of polyethylene. The opening end part on the rear end side of this jacket cover 19 is fixed with a thread-like member 23 wound on a recessed step of a ring-shaped connecting fixing member 22 having a sufficient strength and interposed on the outer periphery of a later described tip block 21 near the boundary with a coating tube 20 on the outer periphery of the curved part 4 and with a bonding agent so as to be kept liquid-tight and to prevent the jacket cover 19 from being pulled off the step. That is to say, the inside diameter of the periphery of the end part on the rear end side of the above mentioned jacket cover 19 is smaller. This smaller diameter part is fitted to a small diameter step of the connecting fixing member 22 around which an elastic soft tube 25 is fitted. This fitted jacket cover 19 is strongly fixed in the end part with the above mentioned thread-like member 23 wound in the position of the recessed step and this wound thread-like member 23 is painted on the outer peripheral recess with a bonding agent 24 to improve the liquid-tightness. A recessed step is formed also on the outer periphery near the front end of the soft coating tube 20 coating the outer peripheries of the curved part 4 and the inserted part 2 in the rear of it through the above mentioned connecting fixing member 22, has a thread-like member 26 wound on it and is painted on the outer peripheral recess with a bonding agent 27 so as to be liquid-tight. Thus, the soft jacket cover 19 on the tip side and the soft coating tube 20 on the outer periphery of the curved part 4 are not connected directly with each other but the ring-shaped connecting fixing member 22 having a sufficient strength is interposed between them. Therefore, the jacket cover 19 and coating tube 20 can be strongly held and, in case they are repeatedly inserted and removed, when the jacket cover 19 on the tip side or the coating tube 20 on the outer periphery of the curved part 4 is worn or broken, only the part will be able to be replaced by unwinding the above mentioned wound thread-like members 23 and 26.

A housing chamber 28 is formed on a hollow tip block 21 covered on the outer periphery with the jacket cover 19 and coating tube 20. Within this housing chamber 28, an ultrasonic wave oscillator 29 transmitting and receiving ultrasonic waves is fixed to the above mentioned tip block 21 with a screw or the like and a rotatable and removable ultrasonic wave mirror 32 is contained as fitted to the tip of a hard first shaft 31 rotated and driven to scan ultrasonic waves as inclined, for example, by 45 degrees with an ultrasonic wave transmitting and receiving surface 30 of this ultrasonic wave oscillator 29. The above mentioned housing chamber 28 is filled with an ultrasonic wave transmitting medium 33. When an aqueous solution of sucrose of a concentration of about 5 to 15% is used for this transmitting medium 33, the respective members will be able to be better prevented from rusting than with saline water or the like, its acoustic impedance will be able to be made substantially equal to that of a living body, therefore ultrasonic waves will be able to be efficiently transmitted, the aqueous solution will be lower in the loss component to the propagation of ultrasonic waves than oil or the like and therefore the reduction of the intensity of the ultrasonic wave beam during the propagation will be able to be prevented.

A guide groove 34 is formed on the base side of the above mentioned mirror 32 so that the mirror can be fitted to and removed from the first shaft 31 by being inserted and removed in the direction at right angles with the shaft 31 and can be removably fixed to the shaft 31 with screws screwed with screw holes.

A cable 35 transmitting signals for transmitting and receiving ultrasonic waves is connected to the above mentioned ultrasonic wave oscillator 29, is inserted and extended through the curved part 4 and inserted part 2 to the operating part and is finally connected with an external ultrasonic wave indicating device through an electric cable 8 from the operating part 7 side.

A window 36 for transmitting and receiving ultrasonic waves is formed by making an opening in a part of the side wall of the housing chamber 28 formed of the tip block 21 around the above mentioned mirror 32 so that the ultrasonic wave beam sent out of the transmitting and receiving surface 30 of the ultrasonic wave oscillator 29 will be reflected by the mirror 32 and will be emitted out of the opening, that is, the transmitting and receiving window 36 in the tip block 21 through the jacket cover 19 and, on the other hand, a part of the ultrasonic waves reflected by the discontinuous boundary surface of the external acoustic impedance will be reflected by the mirror 32 and will be received by the ultrasonic wave oscillator 29.

The above mentioned transmitting and receiving window 36 is also a mirror fitting and removing opening through which the above mentioned mirror 32 can be removed or fitted.

The above mentioned mirror 32 is fitted to the tip of the hard first shaft 31 screwed with a following second shaft 37 rotatably borne by a bearing 38. This bearing 38 contacts on the rear end side with a locking part or stop projecting inside the tip block 21 and a recess formed on the second shaft 37 and is supported at the other end with a ring-shaped lock screw 39 so as not to move forward and rearward.

Sealing members 40 substantially U-shaped in the cross-section are annularly fitted in an annular space between the outer peripheral surface of the above mentioned hard first shaft 31 and the inner wall surface of the tip block 21. The respective sealing members 40 are fitted into a recess between shaft 31 and tip block 21 so that the arms of the U-shaped members are biased against the inner and outer surfaces of the recess. On the other hand, a grease charged chamber 41 formed between one sealing member 40 having the U-shaped recess and the other sealing member 40 is charged with such grease as Moricoat Grease to prevent the transmitting medium 33 from leaking to the bearing 38 side and to control the friction resistance in case the shaft 31 in contact with the sealing members 40 rotates so that the shaft 31 may smoothly rotate.

Many articulated frames 42 rotatably connected in the pivoted parts on both sides adjacent to each other are contained within the curved part 4 coated with the above mentioned coated tube 20 and the articulated frame positioned at the tip is fixed to the outer peripheral surface at the rear end of the tip block 21. A later described pair of operating wires inserted from the hand side are secured at the tips to both sides of the articulated frame 42 positioned at the tip so that the curved part 4 can be curved rightward and leftward by drawing and relaxing these operating wires in case the incised window 5 is positioned in the upper part. On the other hand, a soft driving shaft 44 connected at the front end with the above mentioned hard second shaft 37 and at the rear end with a later described hard driving shaft is inserted through a soft tube 45 made, for example, of Teflon low in the friction coefficient in the inside hollow part of this curved part 4.

The above mentioned soft driving shaft 44 is formed of two inside and outside wound layer coils. These inside and outside coils are wound reversely to each other so that the contour will not be deformed with the rotating direction and the rotation will be able to be effectively transmitted even when curved. This soft driving shaft 44 and the above mentioned hard second shaft 37 are connected with each other through a connecting pin 46. This connecting means is as follows. The above mentioned soft driving shaft 44 is hardened in the tip part by such as fusing and a pin fitting hole 47 fitting the above mentioned pin 46 is made in the diametrically direction in the hardened part. The above mentioned hard second shaft 37 is formed to be small in the diameter in the rear end part so as to be inserted into the tip part of the above mentioned soft driving shaft 44. Further, a pin fitting hole 48 communicating with the pin fitting hole 47 made in the above mentioned soft driving shaft 44 is made in the rear end part of this hard second shaft 37. The pin 46 is fitted and fixed through both pin fitting holes 47 and 48 made in the above mentioned soft and hard second shafts 44 and 37 to connect these soft and hard driving shafts 44 and 37 with each other.

Figure 4:
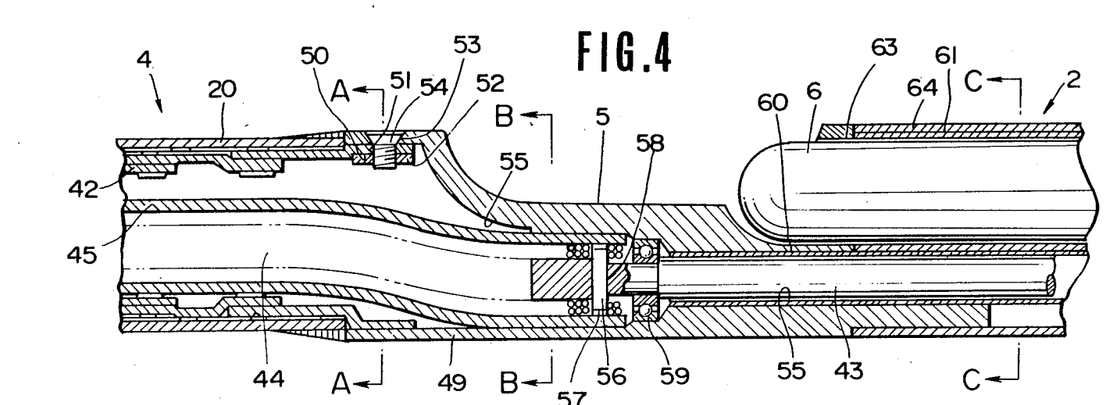
FIG. 4 is a magnified sectioned view showing the vicinity of the curved part and inserted part tip in FIG. 1.
Figure 5:
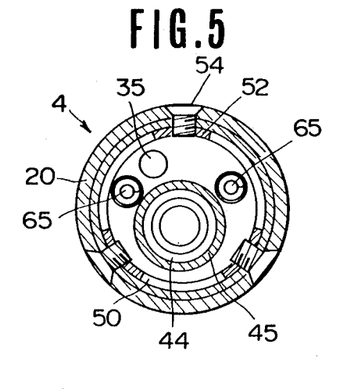
FIG. 5 is a sectioned view on line A—A in FIG. 4.
Figure 6:
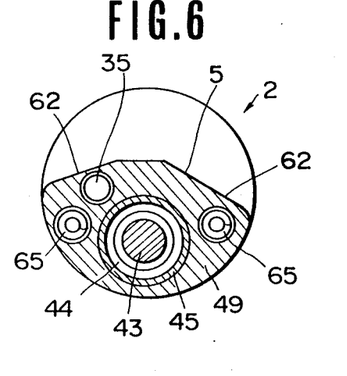
FIG. 6 is a sectioned view on line B—B in FIG. 4.

The above mentioned curved part 4 and the inserted part 2 following it are connected with each other through a connecting member 49 as shown in FIG. 4. In FIGS. 4 and 5, an expanded step 50 is formed in the rear part of the articulated frame 42 positioned in the rearmost position of the curved part 4, screw inserting holes 51 opening in the diametric direction are made, for example, in three places in the peripheral direction in this step 50 and nuts 52 communicating with the above mentioned screw inserting holes 51 are dropped and secured within this step 50. These nuts 52 are formed to be arcuate so as to be in close contact with the inner peripheral surface of the above mentioned step 50 and are completely dropped into the above mentioned step 50 to prevent the above mentioned curved part 4 from becoming narrow in the rear part.

On the other hand, in the rear of the above mentioned articulated frame 42, the following connecting member 49 is fitted in the tip part to cover the outer periphery of the above mentioned step 50 and, for example, three counter sunk portions 53 communicating with the above mentioned screw inserting holes 51 are made in this tip part. Screws 54 are screwed with the screw inserting holes 53 in the tip part of this connecting member 49, the screw inserting holes 51 in the rear part of the above mentioned articulated frame 42 and the nuts 52 as made to communicate with one another to connect the above mentioned curved part 4 and inserted part 2 with each other through the connecting member 49 at the tip of the inserted part. Within this connecting member 49, the driving shaft inserting hole 55 is made in the lengthwise direction and the soft driving shaft 44 inserted through the above mentioned soft tube 45 is inserted in the rear part from the front side and is connected to the following hard driving shaft 43 in the course of this driving shaft inserting hole 55. This soft driving shaft 44 and hard driving shaft 43 are connected with each other through a connecting pin 56. This connecting means is as follows. That is to say, the above mentioned soft driving shaft 44 is hardened in the rear end part by such as fusing and a pin fitting hole 57 fitting the above mentioned pin 56 is made in the diametric direction in the hardened part. The above mentioned hard driving shaft 43 is formed to be smaller in diameter in the tip part so as to be inserted into the rear end part of the above mentioned soft driving shaft 44. Further, a pin fitting hole 58 communicating with the pin fitting hole 57 made in the above mentioned soft driving shaft 44 is made in the tip part of this hard driving shaft 43.

The pin 56 is fitted and fixed in both pin fitting holes 57 and 58 made in the above mentioned soft and hard driving shafts 44 and 43 as made to communicate with each other to connect these soft and hard driving shafts 44 and 43 with each other. This hard driving shaft 43 is rotatably borne by a bearing 59.

The above mentioned hard driving shaft 43 is coated with an outer skin 60 made, for example, of Teflon low in the friction coefficient.

The incised window 5 exposing the tip part of the optical sighting tube 6 inserted through the guide tube 61 from the hand side in the rear of the inserted part as mentioned above is formed in the connecting member 49. This incised window 5 is incised to be of a sector having right and left downward sloped surfaces 62 of a proper length in the axial direction on the upper outer periphery of the connecting member 49. A communicating hole 63 communicating with the optical sighting tube guide tube 61 is formed in the rear part of this incised window 5. As understood from FIGS. 4 and 7, the communicating hole 63 of the above mentioned connecting member 49 and the optical sighting tube guide tube 61 fitted through the inserted part 2 are provided in positions located on the upper side with respect to the axial center of the inserted part 2 and deviated rightward as seen from the hand side (the operator side). The optical sighting tube 6 is inserted from the hand side of the inserted part to the above mentioned incised window 5 through the guide tube 61 within the inserted part and is inserted in the inclined tip part having an illuminating window and observing window directed rightward or leftward and directed upward by about 20 degrees from the horizontal. The optical sighting tube 6 is positioned in the upper part with respect to the axial center of the inserted part in order to attain a visual field as wide as possible by the incised sector in the incisable range without being intercepted by the curved part 4 in front of the incised window 5. Further, the incised window 5 is provided on the upper side opposite the above mentioned transmitting and receiving window 36 so that an organ extending from the lower side to the upper side will not obstruct the visual field by the optical sighting tube 6 in case the above mentioned transmitting and receiving window 36 in the jacket cover 19 on the outer periphery of the ultrasonic wave probe head 3 is introduced into a body cavity and is contacted with (for example) the upper surface of the organ to be diagnosed. Further, the optical sighting tube 6 can be arranged as directed rightward and leftward so as to be able to widely observe both directions. The optical sighting tube 6 is arranged as deviated rightward as seen from the operator side with respect to the axial center of the inserted part 2 to prevent particularly the rightward visual field from being obstructed by the inserted part 2. Thus, the visual field particularly rightward as seen from the operator is secured, because, in diagnosing organs within an abdominal cavity, in what part of the skin there are many blood vessels and in what position the organ is located are naturally determined, therefore, the inserting position and the inserting direction are medically determined and therefore, in the normal using state, if the visual field is rightward and the curved part is curved toward this visual field, it will be adapted to the observation of the organ and such operation and observation within the abdominal cavity as of the close contact of the ultrasonic wave probe head with the organ. Further, in the embodiment, the inclined tip of the optical sighting tube 6 can be set leftward and the ultrasonic wave probe head 3 can be curved leftward, because, with only the rightward visual field, a dead angle will be generated depending on the observed position of the organ and it is necessary to put such dead angle into the observed visual field. Therefore, in the ultrasonic wave diagnoses of others than organs within an abdominal cavity, the observed visual field and curving need not be rightward or leftward. Further, in this embodiment, the inclined tip of the optical sighting tube 6 is set to be upward by about 20 degrees from the rightward or leftward horizontal state so as to prevent the lower side of the visual field from being obstructed by the inserted part 2 or a structure coming in from the lower side.

Figure 7:
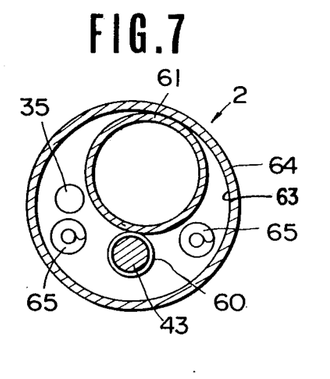
FIG. 7 is a sectioned view on line C—C in FIG. 4.

A jacket tube 64 forming the above mentioned inserted part 2 is fitted and secured by soldering or brazing on the outer periphery of the rear end part of the above mentioned connecting member 49. As shown in FIG. 7, the optical sighting tube guide tube 61 communicating with the optical sighting tube inserting communicating hole 63 of the above mentioned connecting member 49, the hard driving shaft 43 coated with an outer skin, the pair of wires 65 on both sides of this driving shaft 43 and the signal cable 35 are inserted through this inserted part 2.

Figure 8:
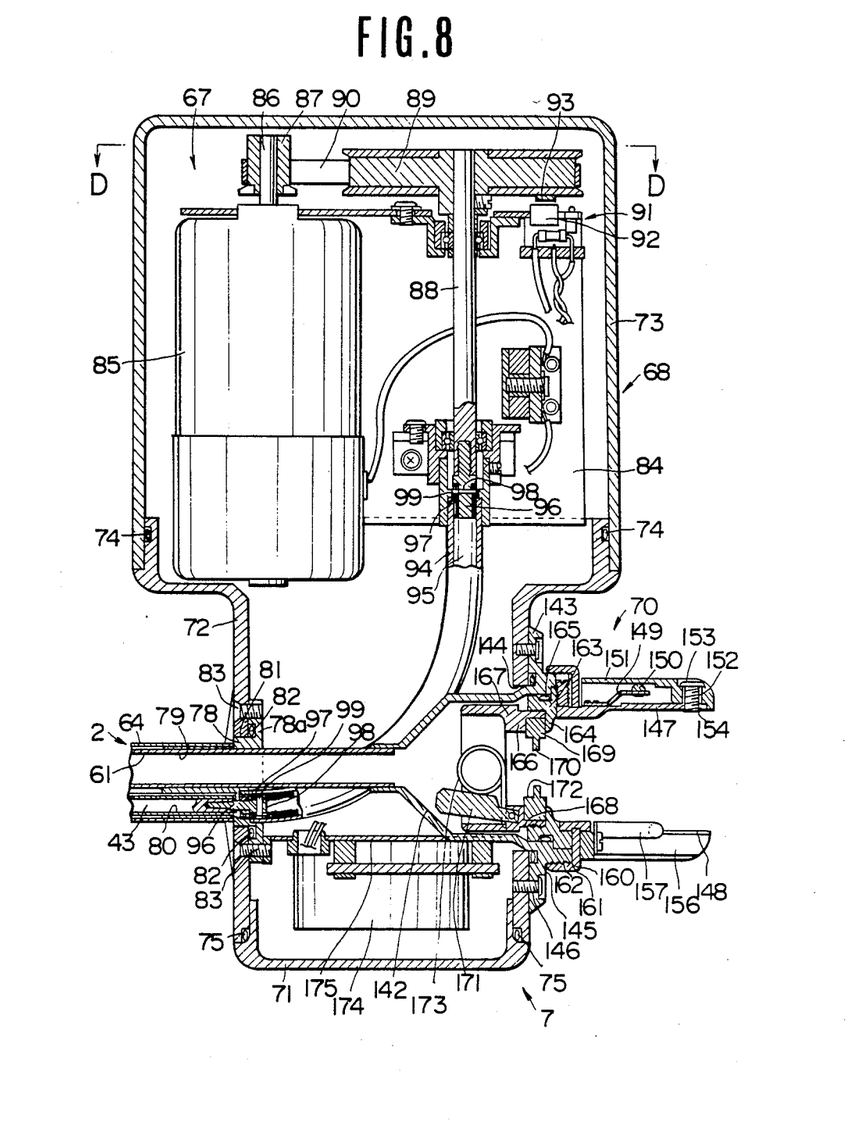
FIG. 8 is a magnified vertically sectioned view of the operating part of the ultrasonic wave probe body.

The operating part 7 is connected to the rear end of this inserted part 2 as shown in FIG. 8. This operating part 7 is formed of a holding part 68 internally fitted with a driving system 67, a curving mechanism 69 arranged on the side of the holding part 68 and an optical sighting tube removably fitting mechanism 70 arranged in the rear of the holding part 68.

The above mentioned holding part 68 consists of a lower case 71, a middle case 72 and an upper case 73 formed to be comparatively large to house the driving system 67 and curving mechanism 69. The cases 71, 72 and 73 are fitted to one another, have O-rings 74 and 75 interposed in the fitting parts so as to be kept liquid-tight and are screwed with screws 76 and 77. The jacket tube 64 of the inserted part is connected to the middle case 72 of this holding part 68 through a connecting member 78. A hole 79 communicating with the optical sighting tube guide tube 61, a hole 80 through which the driving shaft 43 is inserted, wire inserting holes not illustrated and a signal cable inserting hole are made in this connecting member 78. This connecting member 78 has its flange 78a contacted with the inner wall of a connecting member opening 81 formed in the above mentioned middle case 72, has an O-ring 82 interposed between them so as to be liquid-tight and is secured with a screw 83. The above mentioned inserted part jacket tube 64 is fitted to the outer periphery of the connecting member 78 and is secured by soldering or brazing. The optical sighting tube guide tube 61, hard driving shaft, pair of wires 65 and signal cable 35 are extended and inserted from the front into the above mentioned holding part 68. The above mentioned hard driving shaft 43 is borne by the connecting member 78 through a bearing. The driving system 67 is to rotate the ultrasonic wave mirror 32 through the above mentioned driving shafts 44, 43, 37 and 31 to scan ultrasonic waves. A motor 85 connected to a current source through the external electric cable 8 is arranged on a bearing plate 84 screwed to the upper end side of the middle case 72, extended upward and contained in the upper case 73. A pulley 87 is pivoted to an output shaft 86 of this motor 85. A reduction pulley 89 is pivoted to a hard driving shaft 88 borne by the above mentioned bearing plate 84. A belt 90 is stretched between both pulleys 87 and 89.

Figure 12:
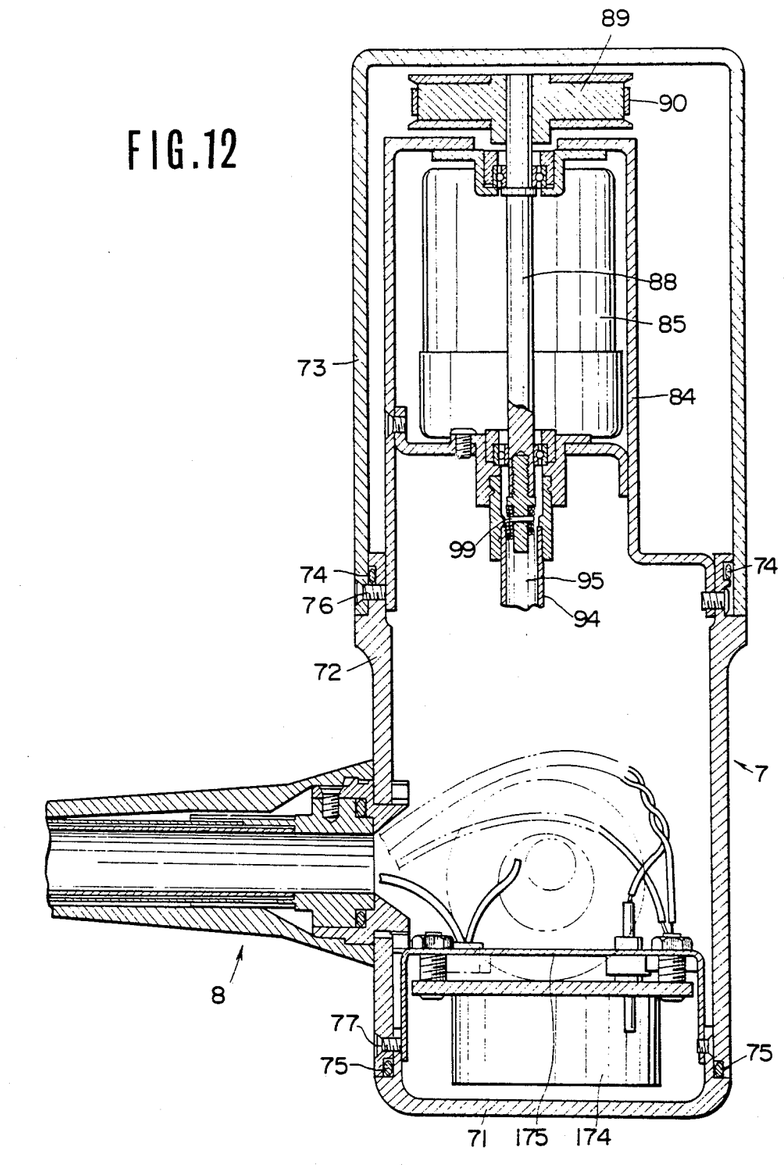
FIG. 12 is a magnified vertically sectioned view of the ultrasonic wave probe body operating part on the electric cable side.

A rotation detector 91 is arranged on the bearing plate 84 in the position opposed to the side of the above mentioned reduction pulley 89. This rotation detector 91 is to measure the direction angle of the scanning ultrasonic wave mirror 32, that is, the ultrasonic wave radiating direction and is to measure the rotation angle of the reduction pulley 89 pivoted to the driving shaft 88. This rotation detector 91 is formed of a detector body 92 transmitting and receiving lights and a light reflecting plate 93 secured to a nonreflecting part of the side surface of the pulley and becoming lines in the diametral direction so that lights may be radiated from the above mentioned detector body 92. On the other hand, the above mentioned light reflecting plate 93 is secured in a proper position on the side surface of the reduction pulley 89 opposed to the above mentioned detector body 92 so that, when the light radiated from the rotation detector body 92 is reflected by this reflecting plate 93, the reflected light is received again by the above mentioned detector body 92 and the rotating position of the above mentioned reflecting plate 93, that is, the rotation angle of the driving shaft 88 is measured, the radiating direction of the ultrasonic waves then will be transmitted to a separately provided indicating device through the above described electric cable 8.

The hard driving shaft 88 of the above mentioned driving system 67 and the hard driving shaft 43 extended into the holding part 68 from the inserted part 2 are connected with each other through a soft driving shaft 95 inserted through a soft tube 94 made, for example, of Teflon low in the friction coefficient. Thus, the hard driving shaft 88 of the driving system and the hard driving shaft 43 out of the inserted part 2 intersecting at right angles with each other are connected with each other through the soft driving shaft 95 without being connected through bevel gears, because the holding part 68 is small, the optical sighting tube guide tube 61 is inserted in the part of connecting them, the optical sighting tube removably fitting mechanism 70 is arranged and therefore the space is made small.

This soft driving shaft 95 is formed by two tubical coils wound in the reverse direction. Joints 96 are arranged at both front and rear ends of this soft driving shaft 95. The soft driving shaft 95 is connected to the hard driving shaft 43 within the above mentioned inserted part 2 and the hard driving shaft pivoting the above mentioned reduction pulley 89 respectively through these joints 96. The above mentioned joints 96 are fitted to both ends of the soft driving shaft 95 as follows. That is to say, both end parts of the above mentioned soft driving shaft 95 are hardened by such fusing or welding as by soldering or brazing or with a bonding agent. Pin fitting holes 97 are made in the diametric direction respectively in these hardened parts. On the other hand, the above mentioned joints 96 in which pin fitting holes 98 commucating with the pin fitting holes 97 of the above mentioned soft driving shaft 95 are made in the diametral direction are inserted into both hardened end parts of the soft driving shaft 95 and are fitted by engaging and fixing the pins 99 in the above mentioned pin fitting holes 97 and 98 communicating with each other. Further, a male screw is made on the outer periphery of the other end part of the joint 96 fitted to the soft driving shaft 95. Screw holes are formed on the inner peripheries of the rear end part of the hard shaft 43 out of the above mentioned inserted part 2 and the tip part of the hard driving shaft 88 pivoting the above mentioned pulley 89. These joints 96 are screwed and connected with the hard driving shaft 43 out of the inserted part 2 and the hard driving shaft 88 rotating the pulley 89. By the way, the joints 96 of the soft driving shaft 95 can be connected with both driving shafts 43 and 88 not only through such screwing as is mentioned above but also through keys, pins or the like.

Figure 13:
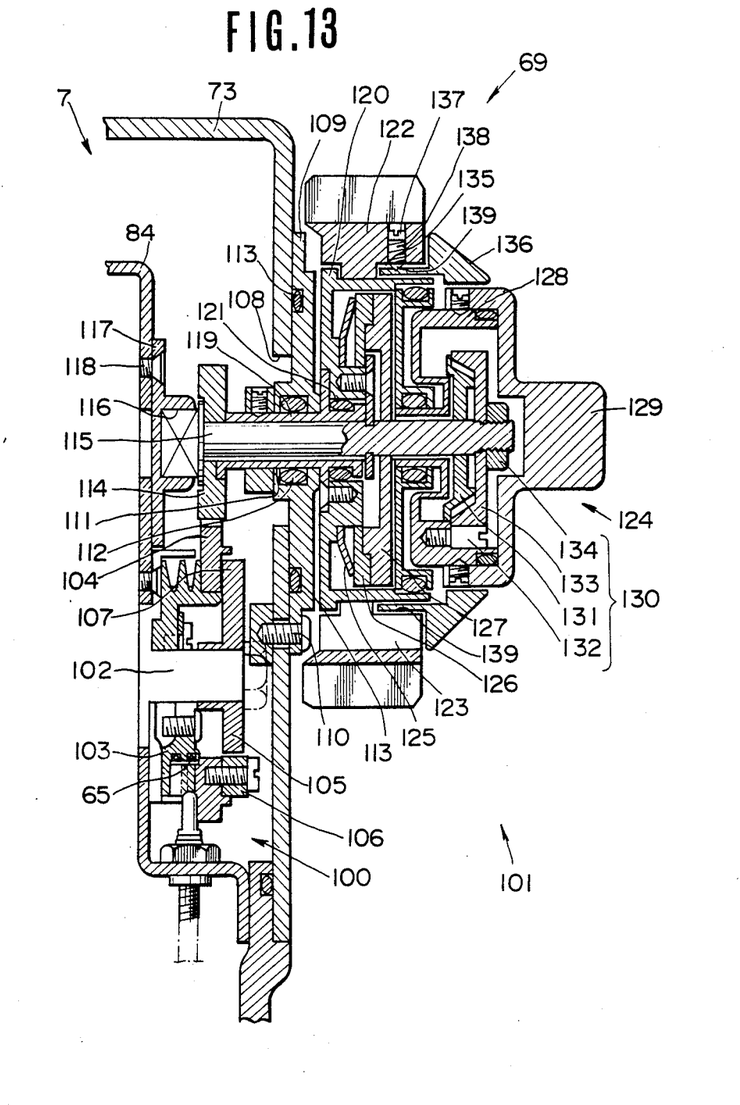
FIG. 13 is a magnified vertically sectioned view of the curving mechanism part in the operating part.
Figure 14:
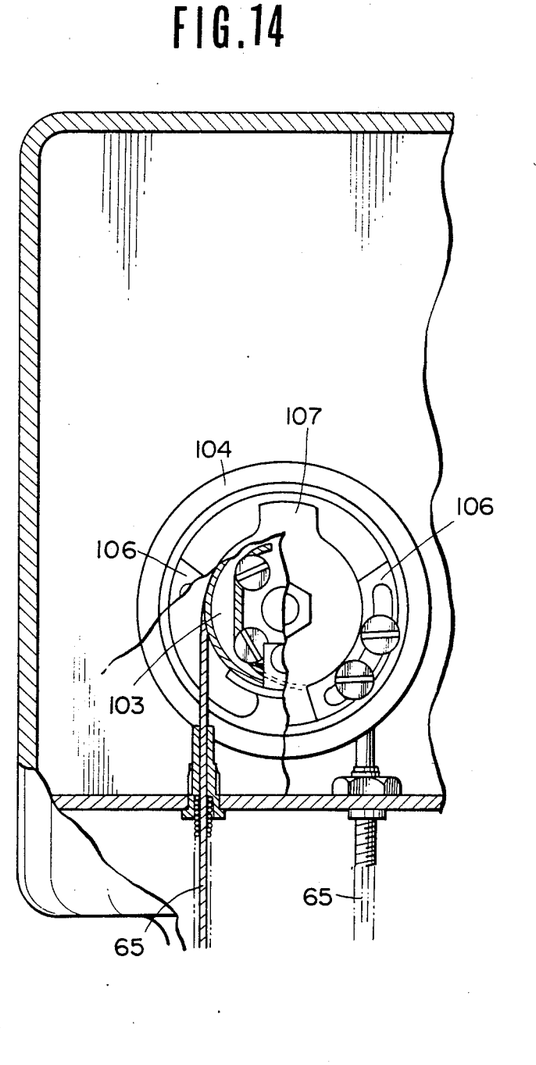
FIG. 14 is a sectioned view showing a wire drum system of the curving mechanism.

By operating the curving mechanism 69, one wire 65 is drawn and the other wire 65 is relaxed to curve the curved part 4 and direct the probe head 3 at the tip of the inserted part 4 rightward or leftward. As shown in FIG. 13, this curving mechanism 69 is formed of a wire drum system 100 and a rotating system 101 and is easy to assemble, disassemble and repair. This wire drum system 100 is arranged inside the right side of the upper case 73. That is to say, this wire drum system 100 is formed of a fixed shaft 102 secured to the side surface of the bearing plate 84 bearing the above mentioned motor 85, a wire winding drum 103 rotatably pivoted to this fixed shaft 102 and winding the wires 65, a gear 104 pivoted to this drum 103 and a pressing member 105. As shown in FIG. 14, the pair of wires 65 are fixed at the rear ends to this drum 103. By the way, in the drawing, the reference numerals 106 denote a pair of regulating plates provided for the drum 103 so as to collide with a projection 107 of the above mentioned pressing member 105 when the drum 103 rotates by a predetermined angle, to prevent the drum 103 from rotating in excess and to regulate the curved degree of the curved part 4 and the drawing distances of the wires 65.

Further, the above mentioned rotating system 101 is inserted on the tip side inside the upper case 73 through an opening 108 formed in the upper case 73 of the holding part 68 and is fitted on the body side to the outside surface of the upper case 73 through a supporting member 109 with a screw 110. This supporting member 108 is plate-shaped, has a hole 111 made in the center and has an O-ring 112 arranged on the inner periphery of this hole 111. Further, the surface of contact of this supporting member 109 with the above mentioned case 73 is made liquid-tight with an O-ring interposed between them. The above mentioned rotating system 101 is made as follows. That is to say, a gear 114 meshing with a gear 104 of the above mentioned wire drum system 100 is rotatably borne on the tip part of the fixed shaft 115 inserted into the above mentioned upper case 73. This fixed shaft 115 is formed to be square in the tip part so as to be fitted and fixed in a fixed member 117 having an engaging hole 116 of the same shape as of it. When this fixed shaft 115 is fitted in the tip part into the fixed member 117, the above mentioned gears 104 and 114 will mesh with each other. This fixed member 117 is arranged and the opening 111 is formed in such positions as satisfy this condition. This fixed member 117 is secured to the side part of the bearing plate 84 with screws 118. Further, a rotating tube body 119 is fitted to the fixed shaft 115 and secures the above mentioned gear 114. A transmitting disk 120 positioned slightly in the rear of the supporting member 109 is secured to this rotating tube body 119 and is extended rearward to be ring-shaped in the outer peripheral part. A boss provided with a hole fitting the above mentioned rotating tube body 119 is formed in the center of this transmitting disk 120. An O-ring 121 is arranged between the fitting hole and this rotating tube body to make them liquid-tight. A curving annular angle knob 122 is secured to the outer periphery of this transmitting disk 120 so that, when this angle knob 122 is rotated, the drum 103 on the above mentioned wire drum system 100 side will rotate clockwise or counterclockwise to draw or relax the above mentioned pair of wires 65 to curve the curved part 4. A groove 123 inserting the above mentioned screw 110 to secure the above mentioned supporting member 109 to the upper case 73 is formed in the inner periphery of this angle knob 122. The above mentioned rotating system 101 is provided with a locking mechanism 124 to lock the rotation of the above mentioned angle knob 122. This locking mechanism 124 comprises a spring member 125 secured to the back surface of the above mentioned transmitting disk 120 and resiliently biased rearward, a sliding contact member 126 in sliding contact with this spring member 125, a pressing member 127 pressing this sliding contact member 126 forward, a movable member 128 advancing this pressing member 127 and an engaging member 129 securing this movable member 128 and arranged in the rear of the angle knob. A spiral groove and a projection engaging with this spiral groove are formed on the contact surfaces of the above mentioned movable member 128 and fixed shaft 115 so that, when the above mentioned engaging member 129 is rotated, the above mentioned movable member 128 will advance along the fixed shaft, this movable member 128 will advance the pressing member 127 and the pressing member 127 will press the sliding contact member 126 against the above mentioned plate spring 125 to lock the rotation of the transmitting disk 120 with the friction force produced there and to prevent the rightward or leftward curved part 4 from returning. This locking mechanism 124 is provided with a stopper mechanism 130 to prevent the lock from locking in excess. When the ultrasonic wave probe body is pulled out of a body cavity, in case the curved part 4 remains curved and is strongly locked as curved, the body cavity interior will be hurt with this curved part 4. Therefore, the locking is regulated so that the curved part 5 can be returned to be straight by the force of colliding with the body wall or the like. In this stopper mechanism 130, a first bevel gear 131 is secured to the fixed shaft 115, a pin 132 is provided to project on the above mentioned movable member 128 and a second bevel gear 133 having a projection to collide with this pin 132 is fitted from the rear to be meshed with the above mentioned first bevel gear 131 and is removably fitted to the fixed shaft 115 with a nut 134 from the rear so that, when the above mentioned engaging member 129 is rotated by a predetermined angle, the pin 132 of the above mentioned movable member 128 will collide with the projection of the second bevel gear 133 to prevent the excess rotation of the engaging member 129, that is, the excess locking of the lock mechanism. By the way, as the second bevel gear 133 is only removably fitted to the fixed shaft 115, when the meshing position of both bevel gears 131 and 133 is reset at any time, the rotation angle of the above mentioned engaging member 129 will be able to be properly set.

Figures 15, 16, 17:
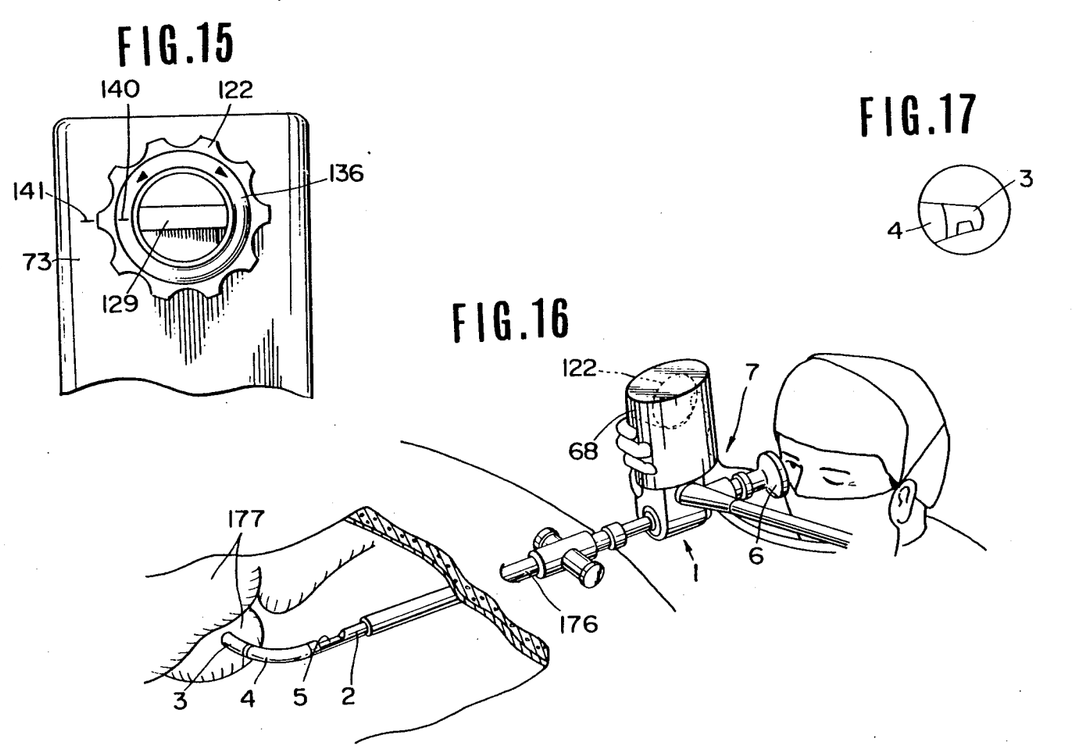
FIG. 15 is a side view showing the curving knob side of the operating part.
FIG. 16 is a perspective view showing this embodiment in use.
FIG. 17 is an explanatory view showing the visual field of the optical sighting tube in use in FIG. 16.

An annular space 135 is formed on the inner peripheral surface on the rear end side of the angle knob 122 of the above mentioned rotating system 101 and a scale plate 136 is rotatably fitted on the annular tip side in this space 135 and is removably secrewed to the angle knob 122 with a screw 137 which is inserted through a diametrical screw hole 138 opened on the outer peripheral side surface of the angle knob 122. This screw 137 is to be locked and fixed at the tip in a peripheral groove 139 made on the contact surface of the above mentioned scale plate 136 with the angle knob 122. As shown in FIG. 15, a (neutral) index 140 is indicated on this scale plate 136 and a fixed index 141 is indicated near the outer periphery of the angle knob 122 of the above mentioned upper case 73 so that the angle knob 122 may be rotated to stretch the curved part 4 to be straight, the above mentioned indices 140 and 141 may be made to coincide with each other and, in this state, the above mentioned scale plate 136 may be fixed to the angle knob 122.

On th other hand, as shown in FIG. 8, the optical sighting tube removably fitting mechanism 70 is arranged in the rear of the above mentioned holding part 68. This optical sighting tube removably fitting mechanism 70 is to be removably fitted and provided within a cover member 142 fitted to the outer periphery of the rear end part of the optical sighting tube guide tube 61. This cover member 142 is substantially funnel-shaped, is fitted on the small diameter side to the outer periphery of the rear end part of the above mentioned optical sighting tube guide tube 61 and has a flange 143 formed on the large diameter rear end side. This flange 143 contacts the outside surface of the above mentioned middle case 72 through the cover member fitting opening 144, is made liquid-tight with an O-ring 145 arranged between them and is secured to this middle case 72 with a screw 146.

Figure 9:
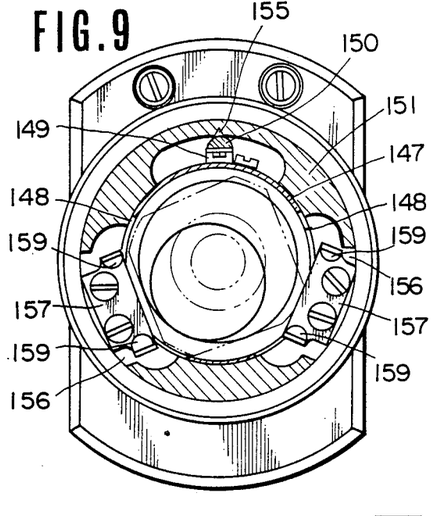
FIG. 9 is a cross-sectioned view of an optical sighting tube removably fitting mechanism part.
Figure 10:
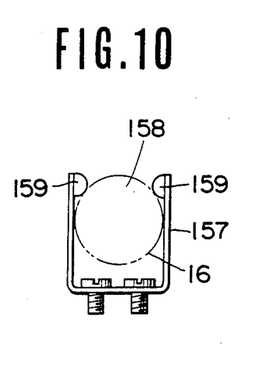
FIG. 10 is a side view of a mouthpiece locking piece in FIG. 8.
Figure 11:
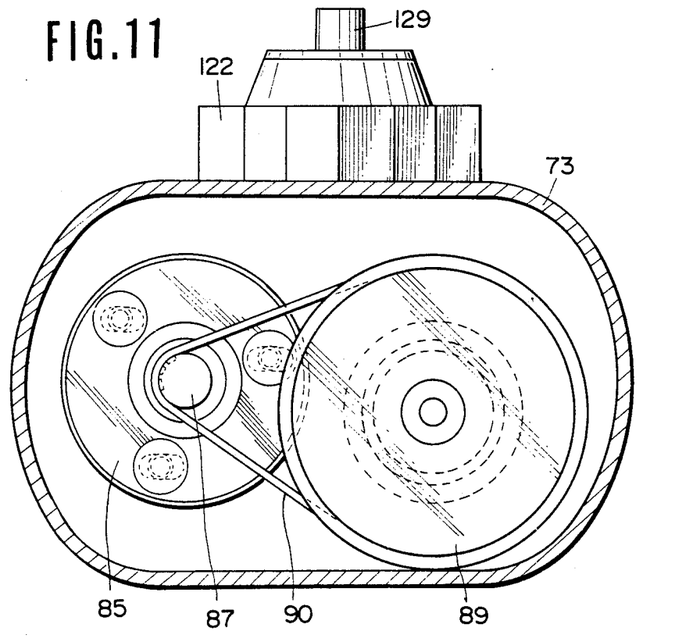
FIG. 11 is a sectioned view on line D—D in FIG. 8.

A tube body 147 through which the above mentioned optical sighting tube 6 is inserted is arranged in the central position of this optical sighting tube removably fitting mechanism 70. As shown in FIG. 9, connector inserting parts 148 through which the light guide connector 16 of the optical sighting tube 6 can be inserted are formed in the axial direction in symmetrical positions separated by 140 degrees from each other on both sides of this tube body 147. These connector inserting parts 148 open at the rear end of the tube body 147 so that the mouthpiece 16 can be inserted from the rear to fix the optical sighting tube 6. A plate spring 149 resiliently biased rearward outward is fitted to the outer periphery of this tube body 147 and a projection 150 is provided to project in the outward end part of this plate spring 149. A rotating member 151 is fitted on the outer periphery of this tube body 147. This rotating member 151 is rotatably fitted to the above mentioned tube body 147. As shown in FIG. 8 a screw hole 152 is made in the diametric direction in the rear part of this rotating member 151. A pin 153 is fitted and screwed in this hole 152 so as to slightly project inward at the tip. This pin 153 is engaged at the tip with a peripheral slot 154 made in the rear part of the above mentioned tube body 147. Therefore, this rotating member 151 can rotate by the width of this slot 154, for example, by about 15 degrees rightward or leftward with respect to the tube body 147 and, at the same time, the optical sighting tube 6 can also rotate in the same manner as borne by the tube body 147 to vary the visual field of the optical sighting tube 6. Further, a groove 155 in which the projection 150 of the above mentioned plate spring 149 is locked in the upper part is formed on the inner periphery of this rotating member 151 so that, when the projection 150 engages with this groove 155, the above mentioned optical sighting tube 6 will be set as directed upward by 20 degrees from the horizontal and will be normally held in this state. As shown in FIG. 9, connector inserting parts 156 communicating with the connector inserting parts 148 of the above mentioned tube body 147 are incised in the axial direction on both sides of this rotating member 151. These connector inserting parts 156 open on the rear end surface of this rotating member 151 and are formed to be substantially U-shaped by having a connector inserting port 158 so that the light guide connector 16 of the optical sighting tube 6 can be inserted from the rear. A connector locking piece 157 shown in FIG. 10 is fitted in each connector inserting part 156, is formed to be substantially U-shaped by having the connector inserting port 158 so that the light guide connector 16 of the optical sighting tube 6 can be inserted, is resiliently biased inward to narrow the above mentioned connector inserting port 158 to bear the the connector 16 of the optical sighting tube 6 and has a pair of projections 159 arranged to project inside the above mentioned connector inserting port 158 and lock the connector 16 on the back surface so as to be able to more securely bear the optical sighting tube 6.

A rotating ring 160 is rotatably fitted on the outer periphery of the tip part of the above mentioned tube body 147, is extended forward on the outer periphery to be short tube (ring)-shaped and has a female screw 161 made on the inner periphery. The female screw 161 of this ring 160 is to be screwed with a male screw 162 made on the outer periphery of the rear end part of the above mentioned cover member 142 and to be screwed to the rear end of this cover member 142.

In front of this rotating ring 160 and inside the cover member 142, a pressing member 163 is fitted to the tip part of the above mentioned tube body 147. A female screw is made on the inner periphery of the tip part of this pressing member 163 and a peripheral projection 164 projecting diametrically inward is provided on the rear end side. Further, an O-ring 165 is arranged between the outer peripheral surface of this pressing member 163 and the cover member 142 to keep them liquid-tight. A fitting member 167 having an optical sighting tube inserting hole 166 is arranged in front of this pressing member 163. A male screw on the inner periphery of the tip part of the above mentioned pressing member 163 is made on the outer periphery of the rear part of this fitting member 167 so as to screw this fitting member 167 to the tip part of the above mentioned pressing member 163. A step 168 of a large diameter is formed inside the rear part of this fitting member 167. A packing 169 is arranged between this step 168 and the projection 164 of the pressing member 163 and has an optical sighting tube inserting hole 170 of a diameter slightly smaller than the outside diameter of the optical sighting tube 6 so as to be in close contact with the outer periphery of this optical sighting tube 6. A valve seat 172 which a later described valve body 171 is to contact is formed in this packing 169.

The above mentioned valve body 171 is arranged in the fitting member 167 as biased to be in close contact with the valve seat 172 by a spring 173. That is to say, the above mentioned valve body 171 is so formed as to be normally in close contact with the valve seat 172 of the packing 169 to close the optical sighting tube passing hole 170, because, when the inserted part 2 of the ultrasonic wave probe body 1 is introduced into a body cavity interior to observe or diagnose it, in case a blood or viscous liquid is deposited on the tip of the optical sighting tube 6 and the visual field is intercepted, it will be necessary to once pull the optical sighting tube 6 out of the inserted part 2 to wipe the stain off the tip surface and also it will be necessary to pull and again insert the optical sighting tube 6 out of and into the inserted part 2 to change the visual field of the optical sighting tube from rightward or leftward to leftward or rightward and therefore, when the above mentioned optical sighting tube 6 is pulled out of the inserted part 2, the gas fed in advance, for example, into an abdominal cavity will have to be prevented from leaking out.

In the thus formed optical sighting tube removably fitting mechanism 70, when the rotating ring 160 is rotated so as to be removed from the cover member 142, not only the packing 169 but also the entirety will be removed from this cover member 142 and will be able to be washed or sterilized.

The signal cable 35 inserted through the inserted part 2 is connected to a head amplifier 174 screwed to the upper end side of the lower case 71, extended upward and contained in the middle case 72. The signal from the ultrasonic wave probe head 3 is amplified here with a low noise and is then fed to the separately provided indicating device through the electric cable 8 projecting out of the side surface of this holding part 68 to indicate an image by ultrasonic waves. This head amplifier 174 is below the middle case 72 or within the lower case 71, that is, in a position reverse to the above mentioned motor 85 and rotation detector 91 on both sides of the soft driving shaft 95 and optical sighting tube guide tube 61, is separated and is hung on the lower surface of a base plate 175 forming a shield vessel so as to reduce as much as possible the influence by the high frequency noise or the like from the motor 85.

According to the thus formed embodiment, first of all, the optical sighting tube 6 as directed rightward or leftward and directed upward by about 20 degrees from the horizontal is inserted from the optical sighting tube removably fitting mechanism 70 provided in the rear of the operating part 7 of the ultrasonic wave probe body 1 and the light guide mouthpiece 16 of the optical sighting tube 6 is engaged with the mouthpiece inserting parts 148 and 156. At this time, the packing 169 within the optical sighting tube removably fitting mechanism 70 will be in close contact with the outer periphery of the optical sighting tube 6 and the above mentioned mouthpiece 16 will be securely borne by the holding force of the U-shaped mouthpiece locking piece 157 fitted to the above mentioned optical sighting tube removably fitting mechanism 70 and the pair of projections 159 arranged in these mouthpiece locking pieces 157.

Then, as shown in FIG. 16, when the operator holds the holding part with one (right) hand and inserts the inserted part 2 into a body cavity, for example, an abdominal cavity through a trocar 176 with the surface of the thumb applied to the angle knob 122 arranged on the side of the holding part 68, if the diagonally sighting type optical sighting tube 6 is introduced into close contact with a desired organ 177 while observing the rightward or leftward diagonal front and sighting the ultrasonic wave probe head 3 within the visual field as shown in FIG. 17 by curving the curved part 4 rightward or leftward and ultrasonic waves are transmitted and received in the form of a sector, an ultrasonic wave fault image for the organ 177 will be able to be indicated in the external indicating device to be observed or diagnosed.

In this case, the optical sighting tube 6 is positioned in the upper part of the inserted part 2 so that the visual field through the observing window at the diagonally sighting tip of the optical sighting tube 6 may not be intercepted by the structure coming in to the outer periphery of the side part from the lower part of the inserted part and, as the optical sighting tube 6 is fitted as deviated righward on the upper side from the center axis, the particularly often used right side visual field will not be intercepted by the outer periphery itself of the inserted part 2 (curved part 4) in front of the incised window 5 and therefore such object as a desired organ will be able to be observed in a well seen state. Also, as the angle of the visual field direction can be varied by rotating the optical sighting tube 6 fitted in the optical sighting tube removably fitting mechanism 70 provided in the operating part 7 together with the rotating member 151 by the width of the slot 154, that is, by about 15 degrees and the visual field direction of the fitted optical sighting tube 6 is directed upward by about 20 degrees, even if such projection as an organ is interposed between the above mentioned incised window 5 and the ultrasonic wave probe head 3 in contact with an object positioned in the curved right side or left side front, if the visual field direction is directed further upward by rotating the above mentioned rotating member 151, the influence of the interposed object intercepting the visual field will be able to be reduced and the desired object and the ultrasonic wave probe head 3 will be able to be put into the observed visual field.

Further, in the above mentioned embodiment, as the optical sighting tube 6 can be inserted through the upper side of the inserted part 2 and the incised window 5 is formed from the upper side to both right and left sides of the inserted part 2, if the optical sighting tube 6 inserting direction is changed, the observed visual field will be able to be made in either of the right and left directions. When the rotating member 151 is rotated with the visual field direction as a center, the (predetermined) angular visual field direction in a range of 15 degrees or more will be able to be varied in both upward and downward directions, an observation direction with the observation over a very wide range as a center will be able to be selected and therefore the observation or diagnosis will be made easy.

In case the above mentioned optical sighting tube 6 is pulled off and the fitting direction is changed, the packing 169 will be brought into close contact with the valve seat 172 and the gas will be prevented from leaking out.

By the way, instead of the observing window by incision without providing the above mentioned packing 169 or the like, an observing window which the observing optical system on the tip side of the optical sighting tube 6 faces can be formed by covering the periphery of the above mentioned incised window 5 with a transparent member so that, even in the case of inserting and removing the optical sighting tube 6, the air-tightness will be able to be well kept.

Further, in the explanation of the above mentioned embodiment, the above mentioned optical sighting tube 6 is inserted as directed upward by about 20 degrees from the horizontal and rightward or leftward and is made rotatable vertically vertically by about 15 degrees in this state but the optical sighting tube 6 can be made rotatable by 180° to 360° degrees and can be locked in a proper angular position. Further, in the above mentioned embodiment, the mirror 32 within the ultrasonic wave probe head 3 is rotated to scan ultrasonic waves but the oscillator 29 may be directly rotated to scan ultrasonic waves. The mirror or oscillator may be rocked instead of being rotated.

It is apparent that working modes different in a wide range can be formed without deviating from the spirit and scope of the present invention. Therefore, the present invention is not restricted by the specific working mode except being limited in the appended claims.

I claim:

1. A device for diagnosing body cavity interiors said device comprising:
    (a) an elongated insertion portion for introduction into a body cavity having forward and rear ends, said insertion portion including a guide tube extending along the length thereof, and a window formed in the side of said insertion portion between the forward and rear ends and positioned at one end of said guide tube;
    (b) an ultrasonic wave probe head means positioned at the forward end of said insertion portion, said ultrasonic head means transmitting ultrasonic waves to body tissue and receiving ultrasonic waves reflected from the body tissue;
    (c) a curved portion formed in said insertion portion at a position adjacent said ultrasonic head means;
    (d) optical tube means having forward and rear ends inserted into said guide tube, wherein the forward end of said optical tube means is positioned in the window of said insertion portion such that body tissues may be observed through said optical tube means; and
    (e) optical tube fitting means coupled to the rear end of said insertion portion, said optical tube means being inserted into said insertion portion through said fitting means;
    (f) wherein the longitudinal axis of said guide tube is positioned to the right and above the longitudinal axis of said insertion portion with reference to an observer looking through said optical tube means such that said guide tube is positioned to one side of the middle of said window and wherein the forward end of said optical tube means and said ultrasonic wave probe head means are located on opposite sides of said insertion portion such that when said ultrasonic head means contacts body tissue and said curved portion is curved, the location of the ultrasonic wave probe head means and the contacted body tissue are in the field of view of the forward end of said optical tube means.

2. A device for diagnosing body cavity interiors according to claim 1, wherein said window is formed in the upper side of the insertion portion as a sector having right and left downward sloped surfaces extending in the axial direction of the insertion part.

3. A device for diagnosing body cavity interiors according to claim 2, wherein said optical tube fitting means includes a packing in close contact with the outer periphery of the optical tube means.

4. A device for diagnosing body cavity interiors according to claim 1, wherein said window includes a transparent means for observing forming a sector of the outer periphery of the upper side and right and left sides of the insertion portion.

5. A device for diagnosing body cavity interiors according to claim 1, wherein said optical tube fitting means includes two connector locking pieces in the form of a U biased inwardly at the ends thereof to lock a light guide connector of the optical tube means inserted in the axial direction of the insertion portion.

6. A device for diagnosing body cavity interiors according to claim 5, wherein said connector locking pieces are formed in side peripheral portions of said fitting means.

7. A device for diagnosing body cavity interiors according to claim 6, wherein said respective connector locking pieces are mounted in said optical tube fitting means such that said connector locking pieces can rotate 15° with said optical tube means fitted therein.

8. A device for diagnosing body cavity interiors according to claim 1, wherein said guide tube is rotatably positioned in said insertion portion such that the rotation thereof rotates the area of observation of said optical tube means.

* * * * *